(12) United States Patent
Jordanoska

(10) Patent No.: US 8,553,227 B2
(45) Date of Patent: Oct. 8, 2013

(54) INSPECTION METHOD AND APPARATUS, LITHOGRAPHIC APPARATUS, LITHOGRAPHIC PROCESSING CELL AND DEVICE MANUFACTURING METHOD

(75) Inventor: Cvetanka Jordanoska, Delft (NL)

(73) Assignee: ASML Netherlands B.V., Veldhoven (NL)

( * ) Notice: Subject to any disclaimer, the term of this patent is extended or adjusted under 35 U.S.C. 154(b) by 1121 days.

(21) Appl. No.: 12/486,449

(22) Filed: Jun. 17, 2009

(65) Prior Publication Data

US 2010/0007863 A1 Jan. 14, 2010

Related U.S. Application Data

(63) Continuation of application No. 12/259,536, filed on Oct. 28, 2008, now abandoned.

(60) Provisional application No. 60/996,356, filed on Nov. 13, 2007.

(51) Int. Cl.
*G01J 4/00* (2006.01)
(52) U.S. Cl.
USPC .......................................................... 356/369
(58) Field of Classification Search
USPC .......................................................... 356/369
See application file for complete search history.

(56) References Cited

U.S. PATENT DOCUMENTS

| | | | |
|---|---|---|---|
| 6,191,880 B1 | 2/2001 | Schuster | |
| 7,102,761 B2 | 9/2006 | De Lega et al. | |
| 7,315,382 B2 * | 1/2008 | De Groot | 356/503 |
| 7,359,033 B2 * | 4/2008 | Yamazoe | 355/53 |
| 7,403,289 B2 * | 7/2008 | de Groot | 356/503 |
| 7,692,769 B2 * | 4/2010 | Fukuhara et al. | 355/71 |
| 7,791,727 B2 | 9/2010 | Den Boef et al. | |
| 7,800,733 B2 * | 9/2010 | Op de Beeck | 355/67 |
| 2004/0085544 A1 * | 5/2004 | De Groot | 356/497 |
| 2006/0197934 A1 * | 9/2006 | Yamazoe | 355/71 |
| 2006/0291057 A1 | 12/2006 | Fiolka et al. | |
| 2007/0081139 A1 * | 4/2007 | Fukuhara et al. | 355/71 |
| 2007/0081167 A1 * | 4/2007 | De Groot | 356/503 |
| 2007/0247637 A1 * | 10/2007 | de Groot | 356/511 |
| 2008/0049233 A1 * | 2/2008 | De Groot | 356/511 |
| 2009/0015844 A1 * | 1/2009 | De Groot | 356/511 |
| 2010/0003620 A1 * | 1/2010 | Kawashima | 430/322 |

FOREIGN PATENT DOCUMENTS

| | | |
|---|---|---|
| EP | 1 574 904 A1 | 9/2005 |
| EP | 1 628 164 A2 | 2/2006 |
| JP | 09-184918 A | 7/1997 |
| JP | 2005-538359 A | 12/2005 |
| JP | 2006-060214 A | 3/2006 |
| JP | 2007-527549 A | 9/2007 |

OTHER PUBLICATIONS

Stalder et al., "Linearly polarized with axial symmetry generated by liquid-crystal polarization converters", Optics Letters, vol. 21, No. 23, Dec. 1, 1996, pp. 1948-1950.

(Continued)

*Primary Examiner* — Roy M Punnoose
(74) *Attorney, Agent, or Firm* — Sterne, Kessler, Goldstein & Fox P.L.L.C.

(57) ABSTRACT

An apparatus and method to determine a property of a substrate by measuring, in the pupil plane of a high numerical aperture lens, an angle-resolved spectrum as a result of radiation being reflected off the substrate. The property may be angle and wavelength dependent. The radiation that is reflected off the substrate is radially polarized.

17 Claims, 8 Drawing Sheets

(56) References Cited

OTHER PUBLICATIONS

Jordanoska, Cvetanka, "Inspection Method and Apparatus, Lithographic Apparatus, Lithographic Processing Cell and Device Manufacturing Method", U.S. Appl. No. 12/259,536, filed Oct. 28, 2008.

English language Abstract of Japanese Patent Publication No. 09-184918 A, published Jul. 15, 1997, Japanese Patent Office; 1 page.

English language Abstract of Japanese Patent Publication No. 2006-060214 A, published Mar. 2, 2006, Japanese Patent Office; 1 page.

English translation of Japanese Notice of Reasons for Rejection directed to Japanese Patent Application No. 2008-284915, Japanese Patent Office, mailed Apr. 20, 2011; 3 pages.

* cited by examiner

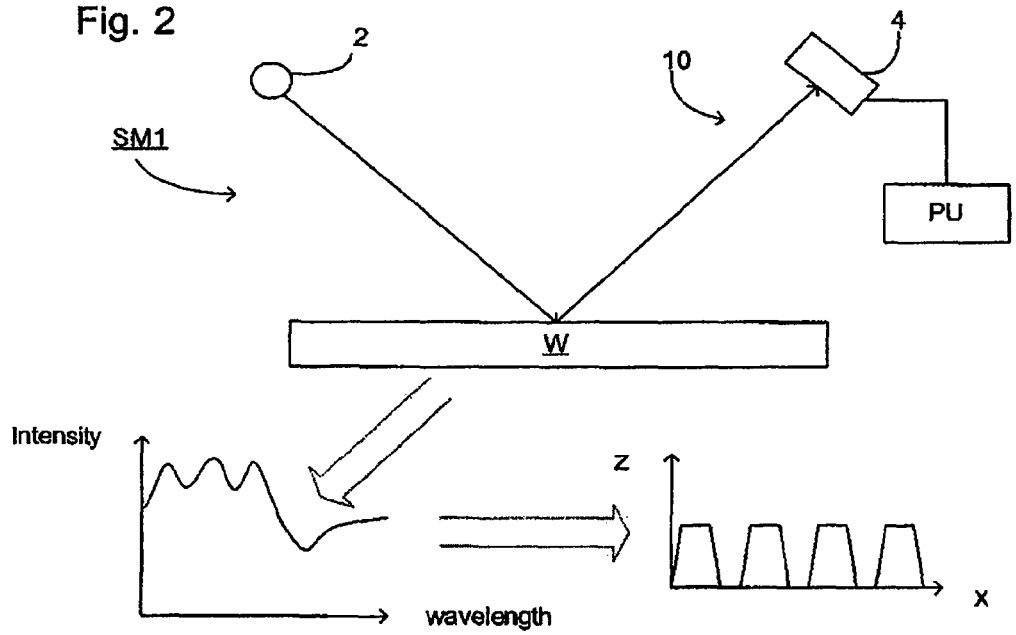
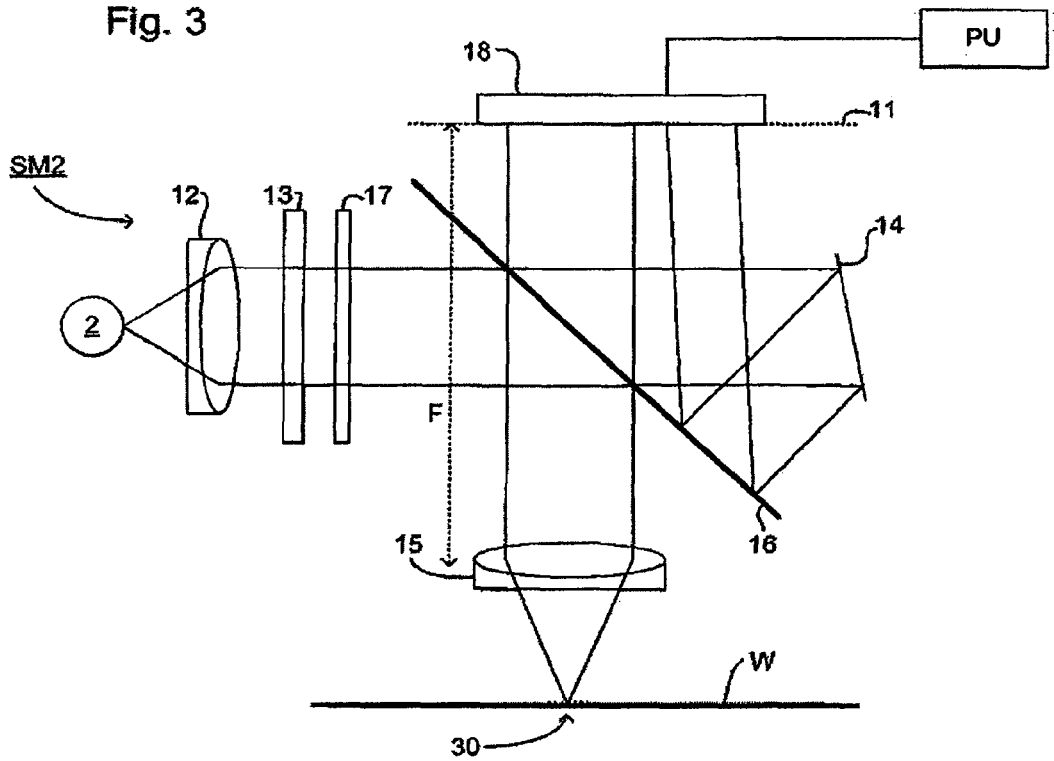

Fig. 9
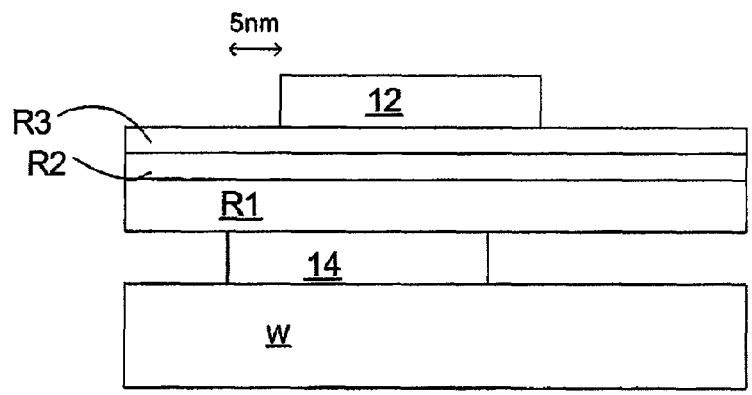
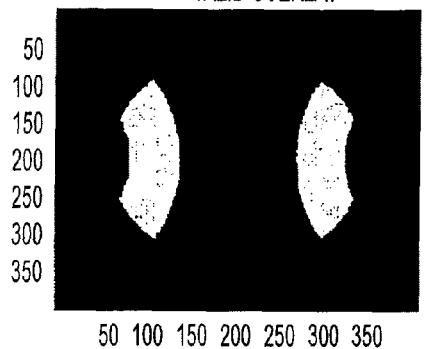
Fig. 10
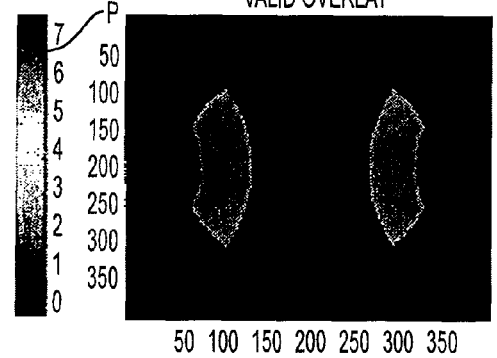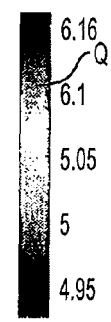
Fig. 11
Fig. 12 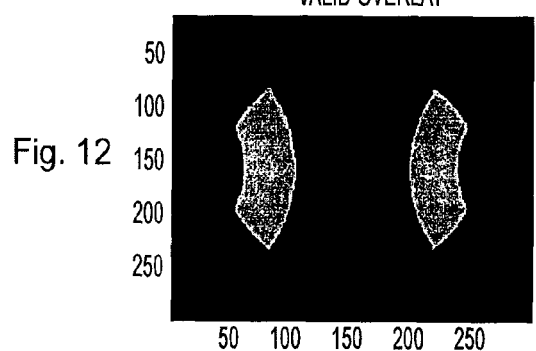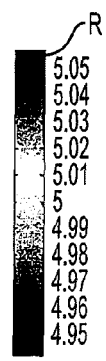

INSPECTION METHOD AND APPARATUS, LITHOGRAPHIC APPARATUS, LITHOGRAPHIC PROCESSING CELL AND DEVICE MANUFACTURING METHOD

CROSS REFERENCE TO RELATED APPLICATIONS

This is a Continuation of U.S. application Ser. No. 12/259,536, filed Oct. 28, 2008 (now abandoned), which claims benefit of under 35 U.S.C. §119(e) to U.S. Provisional Patent Application No. 60/996,356, filed Nov. 13, 2007, which are incorporated by reference herein in their entirety.

BACKGROUND

1. Field of the Invention

The present invention relates to methods of inspection usable, for example, in the manufacture of devices by lithographic techniques and to methods of manufacturing devices using lithographic techniques.

2. Related Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate, which is developed using radiation. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning" direction) while synchronously scanning the substrate parallel or anti-parallel to this direction. It is also possible to transfer the pattern from the patterning device to the substrate by imprinting the pattern onto the substrate or by etching.

In order to monitor the lithographic process, it is desirable to measure parameters of the patterned substrate, for example the overlay error between successive layers formed in or on it. This measurement may take place during the lithographic process, or separately from it, but is usually carried out using a separate metrology apparatus from the lithographic apparatus, as each apparatus involves a not insignificant amount of relative specialism.

The measurement and inspection step after development of the resist, or substrate surface in the case of etching, is referred to as in-line because it is carried out in the normal course of processing production substrates, and typically serves two purposes. First, it is desirable to detect any target areas where the pattern in the developed resist is faulty. If a sufficient number of target areas are faulty, the substrate may be stripped of the patterned resist and re-exposed, hopefully correctly, rather than making the fault permanent by carrying out a process step, e.g., an etch, with a faulty pattern. Second, the measurements may allow errors in the lithographic apparatus, e.g., illumination settings or exposure dose, to be detected and corrected for in subsequent exposures.

However, many errors in the lithographic apparatus may not easily be detected or quantified from the patterns printed in resist. Detection of a fault does not always lead directly to its cause. Thus, a variety of off-line procedures for detecting and measuring errors in the lithographic apparatus are known. These may involve replacing the substrate with a measuring device or carrying out exposures of special test patterns, e.g., at a variety of different machine settings.

There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate, or the structures on the substrate, can be determined. A structure on the substrate that gives rise to a reflected spectrum may be reconstructed, e.g., using real-time regression or by comparison to a library of patterns derived by simulation. Reconstruction involves minimization of a cost function. Both approaches calculate the scattering of light by periodic structures. The most common technique is Rigorous Coupled-Wave Analysis (RCWA), though light scattering may also be calculated by other techniques such as Finite Difference Time Domain (FDTD) or Integral Equation techniques.

Two main types of scatterometer are known. Spectroscopic scatterometers direct a broadband radiation beam onto the substrate and measure the spectrum, intensity as a function of wavelength, of the radiation scattered into a particular narrow angular range. Angularly resolved scatterometers use a monochromatic radiation beam and measure the intensity of the scattered radiation as a function of angle.

One parameter on a target on the substrate surface that needs to be measured is overlay. Overlay is the offset of a structure on one substrate layer with respect to a structure on an earlier layer (i.e., a lower layer or a layer closer to the substrate). If there is an overlay, the overall structure after exposure of all the layers will not be formed accurately and may cause problems for the resulting product. An overlay is measured by inspecting the symmetry of the overall stack or structure. Overlay metrology is based on the measurement of an asymmetry in the angular scatter spectrum. Symmetric structures yield symmetric angular spectra and an asymmetry in the target shows up as an asymmetry in the angular scatter spectrum. This property is the basis of overlay metrology using angle-resolved scatterometry.

The radiation used for the overlay metrology is typically a circular or annular beam. An annular beam is used rather than a circular beam because the overlap in the resultant scattered spectrum of the zeroth order diffraction spectrum with the +first, and potentially higher, diffraction orders is easier to decipher with annular radiation beams and fewer of the available photons are "wasted" or "lost". As it is the parts of the diffraction orders that do not overlap that give the information, the overlapping parts are not used for measurement and are therefore "wasted". Only the first "free order" (i.e., the portion of the radiation that does not overlap) contains useful information about the overlay. However, even using an annular radiation beam may not prevent some of the beam from being lost because as targets get smaller, parts of the annular beam should be discarded if it contains information from neighboring targets or even any off-target surface. The beam may not simply be shrunk to fit smaller target sizes, as information from higher diffraction orders is likely to be lost.

SUMMARY

Therefore, what is needed is an effective system and method to provide a radiation source that provides radiation that can be used with smaller targets to measure overlay without losing diffraction spectra information.

In an embodiment of the present invention, there is provided an inspection apparatus, lithographic apparatus or lithographic cell configured to measure a property of a substrate including or containing a scatterometer configured to measure a property of a substrate. The scatterometer includes a radiation source configured to provide a radiation beam, a high numerical aperture lens, and a detector configured to detect an angle-resolved spectrum of the radiation beam reflected at a plurality of angles from a surface of the substrate, wherein the radiation source is configured to radially polarize the radiation beam.

In another embodiment of the present invention, there is provided a method of measuring a property of a substrate, including providing a radiation beam and printing a pattern onto a substrate. The method continues by measuring, in the pupil plane with a high numerical aperture lens, a reflected spectrum of the pattern, wherein the method further includes radially polarizing the radiation beam.

In a further embodiment of the present invention, there is also provided a device manufacturing method including using a lithographic apparatus to form a pattern on a substrate and determining a value related to a parameter of the pattern printed. This is accomplished by providing a radiation beam, printing a pattern onto a substrate, and measuring, in the pupil plane with a high numerical aperture lens, a reflected spectrum of the pattern, wherein the reflected spectrum is created by reflecting a radially polarized radiation beam from the pattern on the substrate Further embodiments, features, and advantages of the present invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

Embodiments of the invention will now be described, by way of example only, with reference to the accompanying drawings in which corresponding reference symbols indicate corresponding parts. Further, the accompanying drawings, which are incorporated herein and form part of the specification, illustrate the present invention and, together with the description, further serve to explain the principles of the invention and to enable a person skilled in the relevant art(s) to make and use the invention.

FIG. 2 depicts a first scatterometer in, according to an embodiment of the present invention.

FIG. 3 depicts a second scatterometer, according to an embodiment of the present invention.

FIG. 9 depicts a side view of a product with a 5 nm overlay, according to an embodiment of the present invention.

FIG. 10 depicts the overlay pattern (e.g., also known as a valid pixel overlay map) for the product of FIG. 9 using TM polarized radiation, according to an embodiment of the present invention.

FIG. 11 depicts the overlay pattern (e.g., valid pixel overlay map) for the product of FIG. 9 using TE polarized radiation, according to an embodiment of the present invention.

FIG. 12 depicts the overlay pattern (valid pixel overlay map) for the product of FIG. 9 using radially polarized radiation, according to an embodiment of the present invention.

Figure 14:
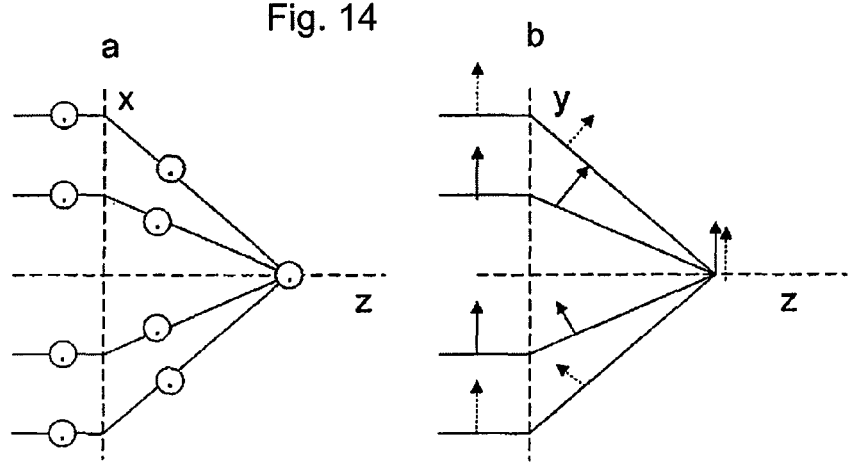

FIGS. 14a-b schematically depict the polarization effects of a radiation beam that travels through a high numerical aperture focusing lens, according to an embodiment of the present invention.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment," "an embodiment," "an example embodiment," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to affect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

Figure 1A:
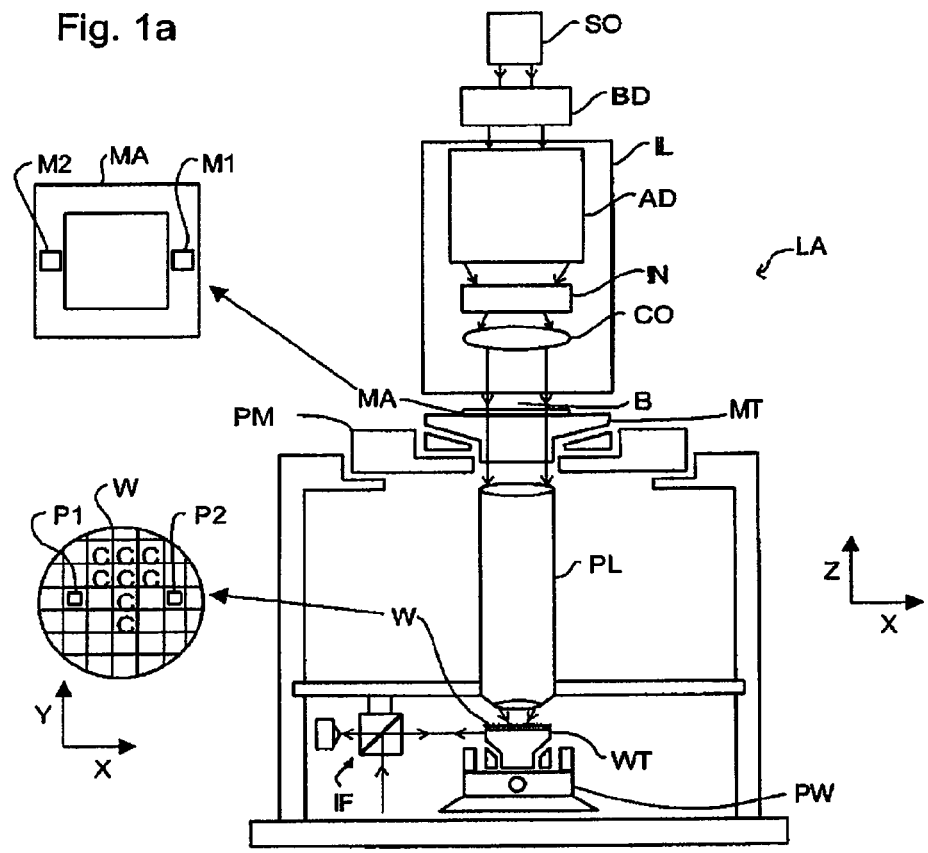
FIG. 1a depicts a lithographic apparatus, according to an embodiment of the present invention.

FIG. 1a schematically depicts a lithographic apparatus in accordance with an embodiment of the invention. The apparatus includes an illumination system (illuminator) IL configured to condition a radiation beam B (e.g., UV radiation or DUV radiation); a support structure or a patterning device support (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist-coated wafer) W and connected to a second positioner PW configured to accurately position the substrate in accordance with certain parameters; and a projection system (e.g., a refractive projection lens system) PL configured to project a pattern imparted to the radiation beam B by patterning device MA onto a target portion C (e.g., including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (e.g., dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1a, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases, the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent, which are commonly referred to as σ-outer and σ-inner, respectively, of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the support structure or the patterning device support (e.g., mask table) MT, and is patterned by the patterning device. Having traversed the patterning device (e.g., mask) MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT may be moved accurately, e.g., so as to position different target portions C in the path of the radiation beam B. Similarly, the first positioner PM and another position sensor (which is not explicitly depicted in FIG. 1a) can be used to accurately position the patterning device (e.g., mask) MA with respect to the path of the radiation beam B, e.g., after mechanical retrieval from a mask library, or during a scan. In general, movement of the support structure or the patterning device support (e.g., mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure or the patterning device support (e.g., mask table) MT may be connected to a short-stroke actuator only, or may be fixed. Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies.

The depicted apparatus could be used in at least one of the following modes:

1. In step mode, the support structure or the patterning device support (e.g., mask table) MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure or the patterning device support (e.g., mask table) MT and the substrate table WT are scanned synchronously while a pattern imparted to the radiation beam is projected onto a target portion C (i.e., a single dynamic exposure). The velocity and direction of the substrate table WT relative to the support structure or the patterning device support (e.g., mask table) MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure or the patterning device support (e.g., mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 1B:
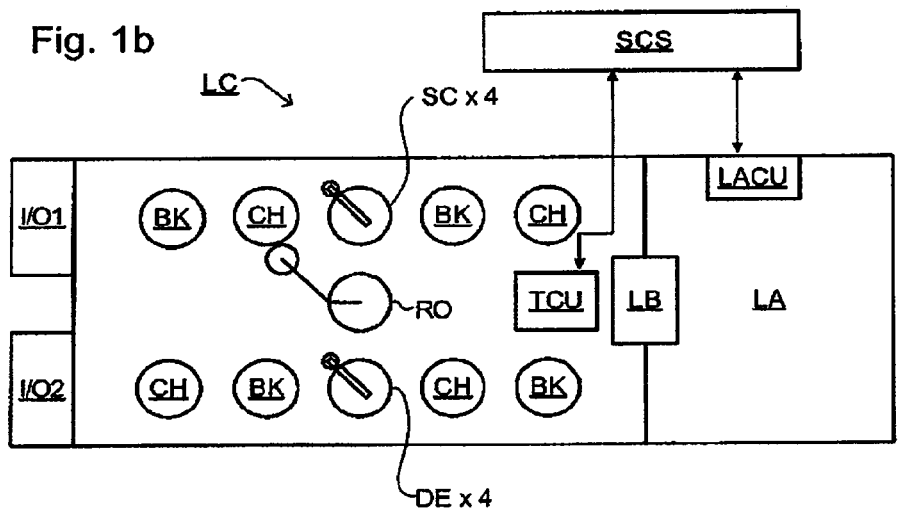
FIG. 1b depicts a lithographic cell or cluster, according to an embodiment of the present invention.

As shown in FIG. 1b, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked, e.g., to improve yield, or discarded, thereby avoiding performing exposures on substrates that are known to be faulty. In a case where only some target portions of a substrate are faulty, further exposures can be performed only on those target portions that are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast such that there is only a very small difference in refractive index between the parts of the resist that have been exposed to radiation and those which have not, and not all inspection apparatus have sufficient sensitivity to make useful measurements of the latent image. Therefore measurements may be taken after the post-exposure bake step (PEB), which is customarily the first step carried out on exposed substrates and increases the contrast between exposed and unexposed parts of the resist. At this stage, the image in the resist may be referred to as semi-latent. It is also possible to make measurements of the developed resist image, at which point either the exposed or unexposed parts of the resist have been removed, or after a pattern transfer step such as etching. The latter possibility limits the possibilities for rework of faulty substrates but may still provide useful information.

FIG. 2 depicts a scatterometer that may be used in an embodiment of the present invention. It includes a broadband (white light) radiation projector 2, which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., by Rigorous Coupled Wave Analysis and non-linear regression or by comparison with a library of simulated spectra as shown at the bottom of FIG. 2. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Another scatterometer that may be used with the present invention is shown in FIG. 3. In this device, the radiation emitted by radiation source 2 is focused using lens system 3 through interference filter 13 and polarizer 17, reflected by partially reflected surface 16 and is focused onto substrate W via a microscope objective lens 15, which has a high numerical aperture (NA), for example, preferably at least about 0.9, and more preferably at least about 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. In one example, the detector 18 may is an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 5. The reference beam is then projected onto a different part of the same detector 18.

A set of interference filters 13 is available to select a wavelength of interest in the range of, for example, about 405-790 nm or even lower, such as about 200-300 nm. The interference filter may be tunable rather than including a set of different filters. A grating could be used instead of interference filters.

The detector 18 may measure the intensity of scattered light at a single wavelength, or narrow wavelength range, the intensity separately at multiple wavelengths or integrated over a wavelength range. Furthermore, the detector may separately measure the intensity of transverse magnetic and transverse electric polarized light and/or the phase difference between the transverse magnetic and transverse electric polarized light.

Using a broadband light source (i.e., one with a wide range of light frequencies or wavelengths—and therefore of colors) is possible, which gives a large etendue, allowing the mixing of multiple wavelengths. The plurality of wavelengths in the broadband preferably each has a bandwidth of $\delta\lambda$ and a spacing of at least 2 $\delta\lambda$ (i.e., twice the bandwidth). A plurality of "sources" of radiation may be different portions of an extended radiation source that have been split using fiber bundles. In this way, angle resolved scatter spectra can be measured at multiple wavelengths in parallel. A 3-D spectrum, for example, such as wavelength and two different angles can be measured, which contains more information than a 2-D spectrum. This allows more information to be measured which increases metrology process robustness. This is described in more detail in European Patent No. 1,628, 164A, which is incorporated by reference herein in its entirety.

The target 30 on substrate W may be a grating, which is printed such that after development, the bars (or lines) of the grating are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

In an embodiment of the present invention, the scatterometer is adapted to measure the overlay of two misaligned gratings or periodic structures by measuring asymmetry in the reflected spectrum and/or the detection configuration, the asymmetry being related to the extent of the overlay. Due to the symmetrical detection configuration, any asymmetry is clearly distinguishable. This provides a straightforward way to measure misalignment in the gratings.

Figure 4A:
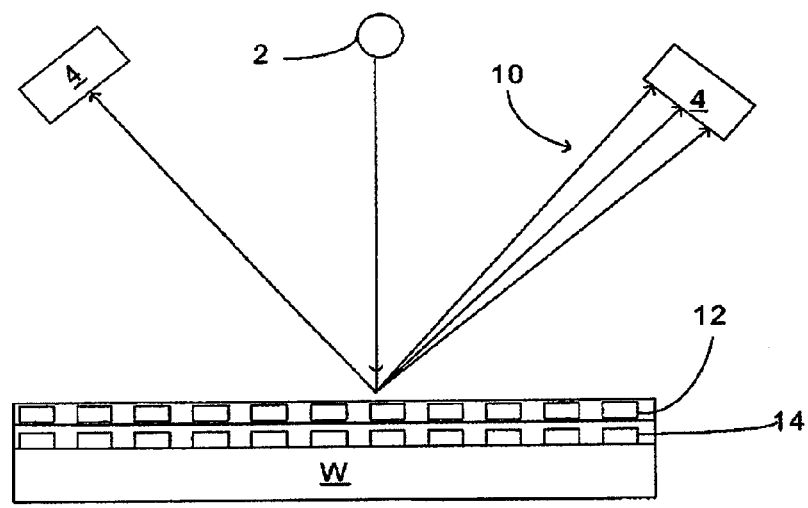
FIG. 4a depicts a scatterometer in use on a product with no overlay according to an embodiment of the present invention.
Figure 4B:
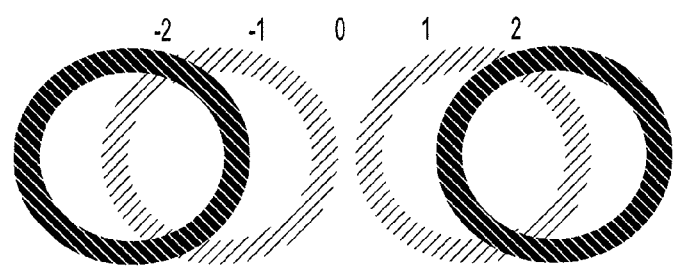
FIG. 4b depicts a diffraction spectrum with zeroth, first and second orders, according to an embodiment of the present invention.

In another embodiment of the present invention, one type of substrate pattern used is shown in FIG. 4a. A grating 14 on a substrate W has a second grating 12 printed on top of it. As can be seen in FIG. 4a, the grating 12 that is superimposed on grating 14 is perfectly in line with grating 14. The resultant diffraction spectrum is shown in FIG. 4b. The circle 0 in the centre of the diffraction spectrum shown in FIG. 4b shows the intensity of the zeroth diffraction order. The similarly shaded overlapping circles labeled 1 and −1 are the +1st and −1st orders of the diffraction spectrum. The darkly shaded circles that overlap with the first order are the +2nd and −2nd diffraction orders. If the gratings 12 and 14 are perfectly in line as shown in FIG. 4a, the intensity shown by the rings in the diffraction spectrum shown in FIG. 4b will symmetrical. Specifically, depending on the type of processor that is used to create the image of the diffraction spectrum, the asymmetry may show up as a variation in shade of the intensity or in darkness of the circle, or any other suitably recognizable parameter that enables an asymmetry to be seen.

Figure 5A:
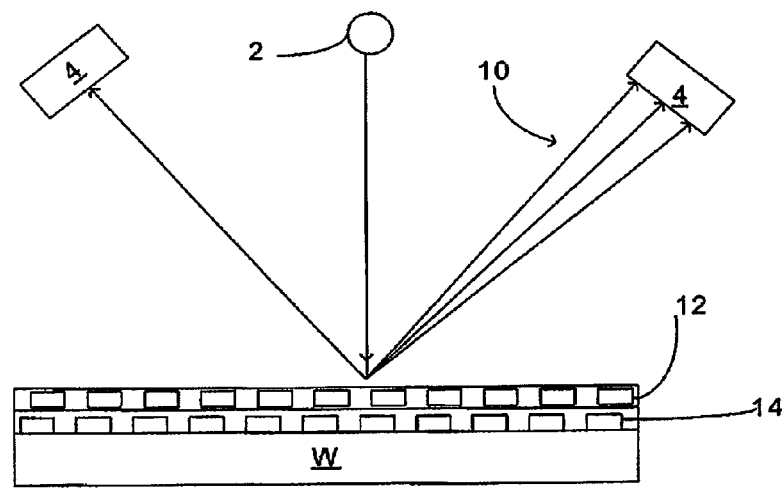
FIG. 5a depicts a scatterometer in use on a product with overlay, according to an embodiment of the present invention.
Figure 5B:
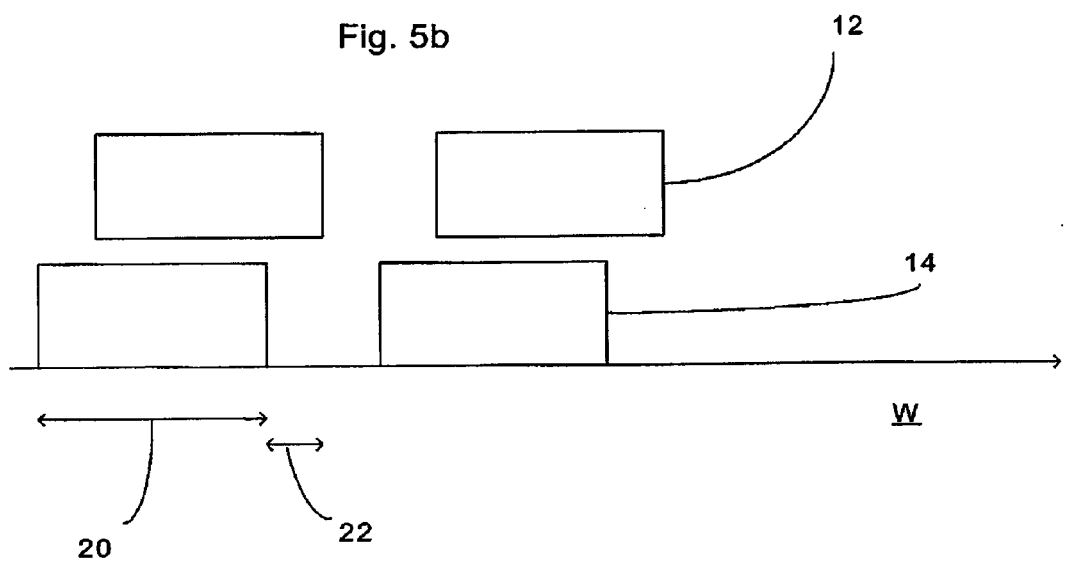
FIG. 5b depicts a closer view of FIG. 5a, according to an embodiment of the present invention.
Figure 5C:
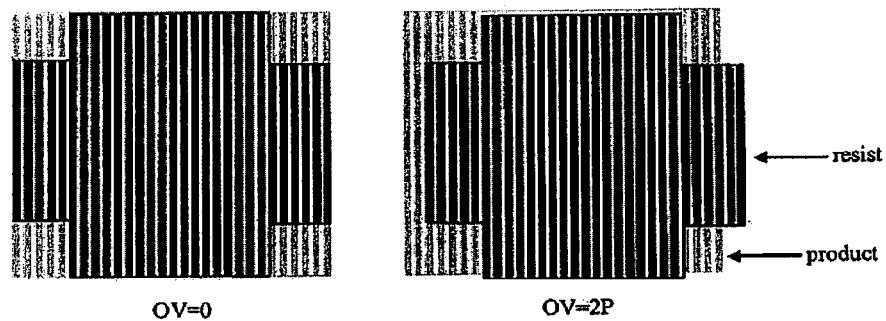
FIG. 5c depicts a top view of a product with overlay, according to an embodiment of the present invention.

FIGS. 5a, 5b and 5c show a grating 14 on a substrate W with a second grating 12 printed on top of it with an offset. The amount by which the grating 12 is offset with respect to grating 14 is known as the overlay 22. FIG. 5a shows the scatterometer and the substrate pattern similarly to FIG. 4a, but with an offset of the second grating 12. FIG. 5b shows a closer view of the two gratings 12 and 14. The width of each bar of the grating is labeled 20 and the width of the offset (i.e., the overlay) is labeled 22. A top view of the overlay is shown in FIG. 5c. The left hand diagram shows no overlay (OV=0) and the right hand diagram shows a resist layer on a product layer, the resist layer having been offset to the right by twice the pitch of the grating (OV=2P). The resultant diffraction spectrum of the scatterometer as detected by detector 4 would look similar to the diffraction spectrum in FIG. 4b, but the area where the first diffraction order does not overlap with the zeroth diffraction order, the first free order, will be asymmetrical. The same applies for the second diffraction orders, though the second diffraction orders are not always visible, particularly if the measurement spot created by the illumination source 2 is very small.

Note that in the embodiment shown in FIGS. 4a and 5a, the radiation source 2 illuminates the object symmetrically with respect to the surface normal and the scatterometry detectors 4 measure scatter radiation from several angles, although a source 2 that illuminates the object from an oblique angle is also possible.

As indicated above, overlay metrology is based on the measurement of an asymmetry in the angular scatter spectrum. Symmetric structures yield symmetric angular spectra and an asymmetry in the target shows up as an asymmetry in the angular scatter spectrum. This property is the basis of overlay metrology using angle-resolved scatterometry.

The two overlapping but misaligned gratings 12 and 14 form one composite asymmetric target. The resulting asymmetry in the angular scatter spectrum is detected with the angle-resolved scatterometer 4 shown in FIG. 5a and used to derive the overlay 22 in the following manner:

Two grating pairs are used with a deliberate bias of +d and −d in, respectively, the first and second pair. In other words, grating 12 is shifted in one direction in one pair (as shown in FIG. 5b) and in the opposite direction in the other pair (not shown). The actual transverse shift between the gratings in each pair is therefore $X_1=OV+d$ and $X_2=OV-d$, OV being the overlay 22.

When the grating pairs are aligned, the overlay is 0 and if the intensity of the illumination incident on the gratings is $I_{ill}$ and the intensity of the radiation reflected off the gratings is $I_{+1}$ in a first direction and $I_{-1}$ in the opposite direction but in the same plane, when the overlay, OV=0, $$I_{+1}=I_{-1}. \quad (1)$$

However, if OV≠0, $$I_{+1} \neq I_{-1}. \quad (2)$$

For a small overlay, the intensity difference is proportional to the overlay:

$$I_{+1}-I_{-1}=K \times OV. \quad (3)$$

K is a constant and is process dependent and therefore unknown.

In order to calibrate the overlay metrology with the scatterometer according to an embodiment of the present invention, two grating targets are used; one with the overlay shown in FIG. 5b and a second with the exact reverse overlay, so the upper grating 12 is displaced to the left rather than the right with respect to the bottom grating 14. The overlay in the first set-up is OV+d (distance 22 in FIG. 5b) and the overlay in the second set-up is OV−d.

So, for OV+d, asymmetry $A_+=K(OV+d)$ and for OV−d, asymmetry $A_-=K(OV-d)$. (5)

The scaling factor K can be eliminated:

$$OV = d \frac{A_+ + A_-}{A_+ - A_-}$$

The overlay can therefore be calculated using measurements of the asymmetry in the angle resolved scatter spectrum.

In an embodiment, it is possible to immerse at least part of the space between the substrate and the detector in liquid, more specifically, the space between lens 15 and the substrate W as shown in FIG. 3. The liquid may be water. This has the benefit of increasing the spatial bandwidth of the medium between the substrate W and the lens 15. This means that a diffraction that would be evanescent in air can propagate in the liquid and be captured by the lens. With immersion of the space, therefore, it becomes possible to detect a higher diffraction order that contains more detailed information about the grating under investigation than with, for example, air in the space.

The numerical aperture (NA) of the scatterometer is preferably at least about 0.9, even about 0.95 or above 1.

Immersing the space between 15 and the object with a high refractive index fluid increases the spatial bandwidth of the medium and allows the propagation of a higher diffraction order for smaller pitches. The smallest pitch that creates a propagating first order spectrum is $$\frac{\lambda}{(2NA)}.$$

Assuming NA equals 1.3 and λ equals about 400 nm, this yields a minimum pitch of about 154 nm. This corresponds to a critical dimension (CD) or reconstructed grating width of approximately 20 to 80 nm. When looking at a profile such as that shown in FIG. 2, the critical dimension is the mean width of a peak and the pitch is the distance from one peak to the next. In this way, not only overlay, but also CD measurement may also be carried out using a scatterometer.

The immersion fluid should have a large index step with respect to, for example, the resist that is on the substrate W. This may allow maximum contrast in the detector image. A possible liquid that fulfils such requirements is water.

In another embodiment, the overlay-determining method described above using a scatterometer and in the CD-determining method also using the scatterometer, the radiation source will typically be linearly polarized because of a combination of the optics that are used to focus the radiation from the source (including optionally a polarizer and/or a beamsplitter) and the fact that the radiation has been reflected from a surface including a grating. However, there are some artifacts associated with using linearly polarized lights that have not been noticed or taken into account before. Those artifacts can affect the results obtained from the overlay measurements. Specifically, impinging a focusing lens through a high numerical aperture causes linearly polarized light to experience polarization effects. The following explanation of what is meant by "polarization effects" refers to FIGS. 14a-b. The radiation beam travels through a high numerical aperture focusing lens. In both FIGS. 14a and 14b, the radiation beam is linearly polarized along the y-axis. The view in FIG. 14a is along the y-axis and the view in FIG. 14b is along the x-axis, across the plane of polarization of the radiation beam. The resultant contribution of the radiation direction shown in FIG. 14b is weaker than the contribution shown in FIG. 14a. This is because the beam which is linearly polarized along the y-axis has its component rays propagating in the xz and yz planes respectively, which contribute differently to the focal field. The focal spot in the yz-plane is elongated in the direction of polarization of the input beam because the rays those propagate in do not add up perfectly at the focus. It can be seen in FIG. 14b that the arrows are not parallel to each other when the incident angle is different, whereas the polarization directions of the rays in FIG. 14a are all parallel to each other and add up properly at the focal point. The vertical electric fields of the rays coming from the top and bottom edges of the lens are tilted with respect to those of the left and right sides, which remain vertical. This asymmetry in the behavior of polarized rays going through a circular lens leads to extra blurring known as a polarization effect.

For linearly polarized light, the energy distribution of linearly polarized components in the direction of the propagation of the beam is not rotationally symmetric. This primarily causes an asymmetric deformation of the focal spot to an elliptical shape. When using an annular aperture, the relative contribution of the longitudinal component is increased and the asymmetry becomes more pronounced.

As a consequence, the intensity distribution at the focused spot on the substrate W or in the pupil plane will lose rotational symmetry. A benefit of rotational symmetry is that a more clearly symmetrical diffraction spectrum will result from rotationally symmetric radiation. The rotationally symmetric spot and reflection spectrum are artifacts (properties) of the radially polarized light. Those artifacts can lead to some benefits for overlay measurements and calculations such as smaller spot size and smoother and more accurate distribution of the pixel values through valid overlay pixel map.

When an annular aperture is used for focusing, only waves that propagate under a large angle to the optical axis contribute to the focal field. For a high numerical aperture and large inner radius of the annular aperture, the electric field vectors for a radially polarized input field are essentially parallel to the optical axis. All rays interfere perfectly and the focused beam is a small rotationally symmetric intense spot with the electric field pointing along the direction of the radiation beam.

Furthermore, the size of a focused measurement spot using linearly polarized light is of the order of 24 µm. However, in order to maximize the amount of product that can be present on a single substrate and also to make that product ever smaller in terms of its pattern, there is a call for measurement target sizes also to be smaller. Using linearly polarized light gives a measurement spot that may be too big to fit on a single measurement target, such that there is noise from the area surrounding the target or even crosstalk from neighboring targets.

Yet furthermore, overlay measurements using linearly polarized light as described above results in a large spread in overlay values in terms of pixel size resulting in a large standard deviation in pixel-by-pixel value. In order to obtain a realistic overlay value, filters often need to be used to block out noise (represented by a bell curve with shoulders, filters being required to take out the shoulders).

Figure 6:
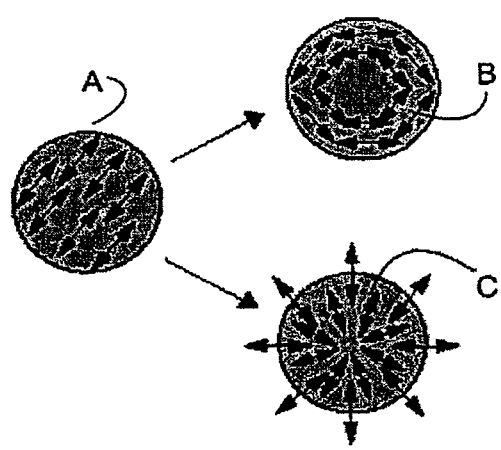
FIG. 6 depicts various polarizations of a radiation beam, according to an embodiment of the present invention.

A further embodiment of the present invention solves the above problems by using radially polarized light as a light source for the scatterometer. Radially polarized light is depicted as radiation beam C in cross-section in FIG. 6. Radiation beam A of FIG. 6 show polarization directions in a linearly polarized radiation beam. Radiation beam B of FIG. 6 shows an azimuthally polarized beam. Radially polarized light has its electric field vectors arranged like spokes of a wheel pointing out from the centre of the beam.

When radially polarized light crosses a lens, the electric field from each part of the beam is tilted symmetrically around the respective part of the beam. Radially polarized light can be focused in this way to a significantly smaller measurement spot than linearly polarized light. For example, a radially polarized light may be focused to a about 200 nm spot. A smaller focused spot contains more information at that spot and therefore more information at the pupil plane on which the spot is focused. Not only does the spot contain more information in a smaller area, the focused spot is rotationally symmetrical. In an embodiment, an optical system is configured to focus the radially polarized radiation beam to a focal spot with a diameter of up to about 200 nm.

Several techniques have been used to create polarized light. There are basically four techniques for polarizing a natural beam of light, i.e., non-polarized light. One technique is based on birefringent or biaxial materials. A second technique is based on the use of dichroic materials such as "polaroid." A third technique employs thin-film technology and it uses Brewster's effect. A fourth technique is based on wire grids or conductive gratings.

The use of birefringent materials to polarize light or radiation is known in the production of birefringent polarizers. Birefringent polarizers may be made from many crystals and also certain stretched polymers. Birefringent materials are materials having a different optical index in one direction compared to another. The degree of difference in the optical index between the two directions varies with the wavelength of the radiation. The difference in index is used to separate beams of one linear polarization from another. Dichroic polarizers are polarizers designed to absorb one polarization and transmit the other one. Most commonly used dichroic polarizers consist of a polymeric sheet stretched to orient its molecules and treated with iodine and/or other materials or chemicals such that the molecules absorb polarization of one orientation. A polarizer device has been developed in which stretched polymer sheets are made birefringent. These stretched sheets reflect one polarization and pass the other. Thin film polarizer technology uses Brewster's effect in which a light beam incident on a surface of a material such as glass, plastic or the like, at Brewster's angle (near 45 degrees) is divided into two polarized beams one transmitted and the other one reflected.

For an image projection system where applications of a polarized light beam are sought, a brighter beam is always desirable. The brightness of a polarized beam is determined by numerous factors, one of the factors being the light source itself. Another factor for a system that employs a polarizer is the angle of acceptance. A polarizer with a narrow or limited acceptance angle cannot gather as much light from a divergent source as a system that employs a wide acceptance angle. A polarizer with large acceptance angles allows flexibility in the design of a projection optical system. This is because it is not necessary for the polarizer to be positioned and oriented within a narrow range of acceptance angles with respect to the light source.

Another desired characteristic for a polarizer is the ability to separate effectively one component of polarization from the other component. This is called the extinction ratio, which is the ratio of the amount of light of the desired polarization component to the amount of light of the undesired polarization component.

Other desired characteristics include freedom of positioning the polarizer in an optical inspection system without diminishing the efficiency of the polarizer and/or introducing additional restrictions on the system such as orientation of the beam etc.

Another polarization technique utilizes a conductive grating or wire grid. A wire grid polarizer is a planar assembly of evenly spaced parallel electrical conductors whose length is much larger than their width and the spacing between the conductive elements is less than the wavelength of the highest frequency light component of the incident light beam. This technique has been successfully used in the radio frequency domain and up to the infrared region of the spectrum. Waves with a polarization parallel to the conductors (S polarization) are reflected while waves of orthogonal polarization (P polarization) are transmitted through the grid. The wire grid polarizer is used mainly in the field of radar, microwaves, and infrared. The wire grid polarizer has also been described in European Patent No. 1574904, which is incorporated by reference herein in its entirety, as being used in an optical projection system for polarizing a light beam for exposure of a resist layer on a substrate as discussed briefly above.

One example of a wire grid polarizer is one that is embedded in a material such as glass and includes an array of parallel, elongated spaced-apart elements sandwiched between first and second layers of the material. The elongated elements form a plurality of gaps between the elements which provide a refractive index less than the refractive index of the first layer. The array of elements is configured to interact with electromagnetic waves in the visible spectrum to reflect most of the light of a first polarization and transmit most of the light of a second polarization. The elements have a period less than 0.3 microns and widths less than 0.15 microns.

The wire grid polarizer technology has not been suggested for use in metrology such as scatterometry, where the measurement radiation beam has a very small wavelength and requires the diameter of its focal spot to be very small, for example, of the order of a few hundred nm.

The polarization state of a wave may be defined by two parameters $\theta$ and $\phi$, where $\theta$ defines the relative magnitudes of TE and TM wave components, and $\phi$ defines their relative phase. The incident wave can be expressed by the following pair of equations:

$$A_{TE} = \cos\theta$$

$$A_{TM} = e^{j\phi}\sin\theta$$

Thus, for $\phi=0$, the wave is linearly polarized at an angle $\theta$. Circular polarization is obtained when $\theta=\pi/4$ and $\phi=\pm\pi/2$. A TE polarized wave is represented by $\theta=0$. A TM wave is represented by $\theta=\pi/2$. TE and TM polarizations are fundamental polarization components.

An embodiment of a radial polarizer has periodic gratings arranged in a radially symmetric pattern. The period of the grating can be selected for a specific wavelength of radiation used and in accordance with other desired parameters. In this embodiment, the gratings are deposited on a substrate, which can be glass or other materials. The gratings may be, for example, a metal such as aluminum, chrome, silver, gold or any material that is conductive at the wavelength the electromagnetic radiation beam. The gratings may also be made, for example, of dielectrics or a combination in a multilayer structure such as, but not limited to, a single layer of $SiO_2$ sandwiched between two layers of $Si_3N_4$ on a fused-quartz substrate. The gratings may also be etched using electron beams, for example, following a pattern transferred to a substrate of GaAs. The gratings may be interlaced to allow smooth transitions of the polarization effects to maintain uniformity of the TE polarization intensity along the diameter of the polarizer. Furthermore, the polarizer may have a disk shape, or a polygonal shape such as, but not limited to, a rectangular shape, hexagonal shape, etc.

Another embodiment of the radial polarizer includes a first layer of material having a first refractive index and a second layer of material having a second refractive index. A plurality of elongated elements (or gratings) azimuthally and periodically spaced apart are disposed between the first layer and the second layer. The plurality of elongated elements interact with electromagnetic waves of light or radiation to transmit transverse electric TE polarization and reflect or absorb TM polarization. The plurality of elongated elements can be made, for example, of silicon dioxide and the first and/or second layers can be made of any material including, for example, quartz, silicone, dioxide, silicon nitride, gallium arsenide etc. or a dielectric material at the wavelength of the electromagnetic beam of radiation. Similarly to the previous embodiment, the spacing or period between the elongated elements can be selected according to the intended use of the polarizer, i.e., for a specific wavelength and in accordance with other parameters in the lithographic system.

A further embodiment of a radial polarizer includes a nematic liquid crystal cell composed of one uniform and one circularly rubbed alignment layer. The local alignment of the LC in the polarization converter is that of a twisted cell, with a twist angle given by the local alignment layers. These twist angles are always smaller than $\pi/2$. When linearly polarized light or radiation is shining through a polarization converter and the polarization direction is parallel or perpendicular to the uniform alignment layer, azimuthally or radially polarized light or radiation emerges on the other side. A more detailed description can be found in Stalder et. al., Optics Letters, volume 21, page 1948, published in 1996, which is incorporated by reference herein in its entirety.

The benefit of using radially polarized radiation in, for example, overlay measurements is that more accurate overlay results are possible with a smaller standard deviation in pixel value. A simulation will be described below.

Radially polarized light or radiation gives a smoother distribution of overlay values for each pixel of an overlay map (a diffraction pattern image) which leads to a much smaller standard deviation and a mean overlay value is closer to a real overlay value. In other words, the overlay value is more accurate.

A yet further benefit of using radially polarized light is that the filters for removing noise are not required because the standard deviation of each pixel value using radially polarized light or radiation is already significantly smaller.

Figure 7:
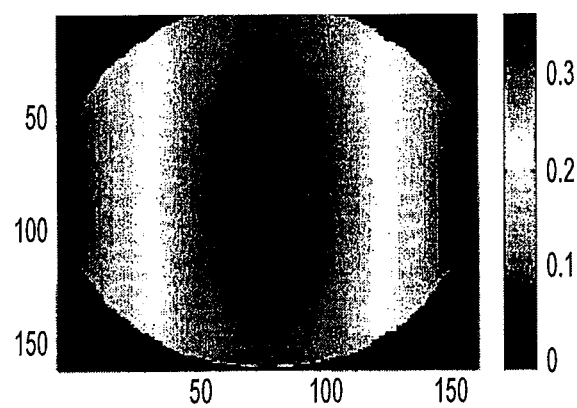
FIG. 7 depicts the reflection spectrum from a flat surface using linearly polarized radiation, according to an embodiment of the present invention.
Figure 8:
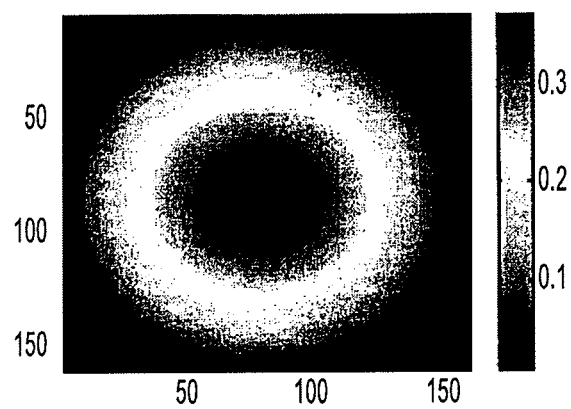
FIG. 8 depicts the reflection spectrum from a flat surface using radially polarized radiation, according to an embodiment of the present invention.
Figure 13:
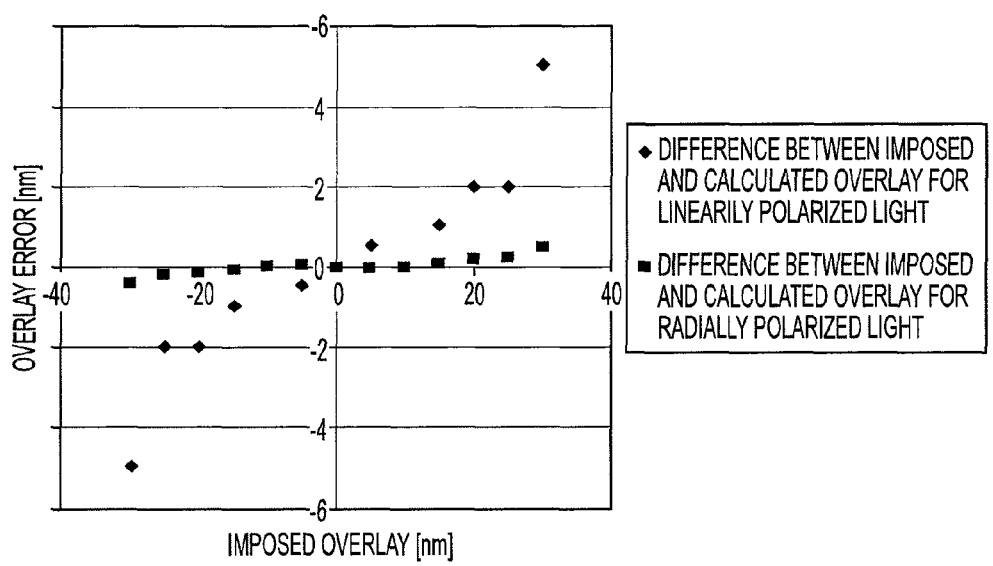
FIG. 13 depicts a graph comparing the use of linearly polarized light with the use of radially polarized light for measuring overlay, according to an embodiment of the present invention.

A comparison of the diffraction spectrum (or a pixel map) of linearly polarized light versus radially polarized light is shown in FIGS. 7 and 8, according to an embodiment of the present invention. FIG. 7 shows the diffraction spectrum of linearly polarized light and FIG. 8 shows the diffraction spectrum of radially polarized light. As can be seen from these figures, linearly polarized light or radiation, although creating a recognizable pattern in which asymmetry may be determined, the resultant pattern using radially polarized light is much clearer. Indeed, it may be said that the diffraction image is perfectly rotationally symmetrical and so any asymmetry will show up more easily. FIG. 13 shows the difference between the accuracy of overlay measurement using linearly polarized radiation (darker diamonds) versus using radially polarized radiation (lighter squares). The actual overlay is on the x-axis and the error in overlay is on the y-axis. It is clearly visible that radially polarized radiation makes fewer errors, even at high overlay values.

In yet another embodiment of the present invention, a simulation was performed using a stack or pattern as shown in FIG. 9. The substrate W is a flat silicon surface with two oppositely bias superimposed gratings with an imposed overlay of about 5 nm. The diffraction patterns of FIGS. 7 and 8 are diffraction patterns of a plane silicon substrate with no pattern and therefore no overlay. Alternatively, FIGS. 10, 11 and 12 show various overlay patterns for the offset of the overlay targets shown in FIG. 9. The bottom grating 14 of FIG. 9 is made of silicon, like the substrate W. The top grating 12 is made of resist. The intervening layers R1, R2 and R3 different materials which are commonly used in the semiconductor industry, such as SiO$_2$, a hard mask, a capping layer or barc. As indicated above, the intentionally imposed overlay is about 5 nm.

The results of the simulations are shown in the following tables: Table 1 shows a result from a simulation of about 600 nm measurement radiation wavelength and an imposed overlay of about 5 nm. Table 2 shows the results of a simulation using about 650 nm measurement radiation wavelength, also with an imposed overlay of about 5 nm. In each table is the result of the mean overlay determined from the diffraction pattern using measurement radiation that had polarization in the TE (Transverse Electric) direction, the TM (Transverse Magnetic) direction and a beam that was radially polarized. FIG. 10 shows the overlay pattern (valid overlay pixel map) obtained with TM-linearly polarized radiation; FIG. 11 shows the overlay pattern (valid overlay pixel map) obtained with TE-linearly polarized radiation and FIG. 12 shows the overlay pattern (valid overlay pixel map) obtained with radially polarized radiation, all for a measurement radiation wavelength of about 650 nm.

TABLE 1

|  | Mean Overlay (nm) | Standard deviation (nm) |
| --- | --- | --- |
| TE polarization | 4.764787 | 0.1325777 |
| TM polarization | 4.7621127 | 1.7154755 |
| Radial polarization | 4.84 | 0.001588 |

TABLE 2

|  | Mean Overlay (nm) | Standard deviation (nm) |
| --- | --- | --- |
| TE polarization | 4.637639 | 0.326421 |
| TM polarization | 4.6365 | 0.3559 |
| Radial polarization | 4.71325 | 0.001 |

As can be seen from the results, in Table 1, the mean overlay result of about 4.84 nm is closer to the actual overlay of about 5 nm, than either linearly polarized radiation beams show. Furthermore, the values for each pixel in the pixel maps shown in FIGS. 10, 11 and 12 are also smoother, indicating that the standard deviation is smaller and so filters are not required to remove noise. Table 2 also shows a more accurate mean overlay result for radial polarization rather than linear polarization, again with a smaller standard deviation.

According to an embodiment of the present invention, the images in FIGS. 10, 11 and 12 show only the free pixel map (first free order) of the first diffraction order with the zeroth diffraction order such that it is specifically only the parts of the rings of FIG. 4b that are within the zeroth diffraction order ring that are measured.

Looking more closely at FIGS. 10, 11 and 12, it can be seen from FIG. 10 that the shade of the overlay image appears somewhere between about 4 and 5 nm at point P. On FIG. 11, the range of the scale is closer to 5 and the shade of the image, labeled as Q, is somewhere between about 4.95 and 5 nm. However, a much more accurate mapping can be created using radially polarized light because the standard deviation is much smaller. The standard deviation is therefore shown on the scale to the right of the overlay pixel map and it can be seen that shade of the overlay is at a point labeled R on FIG. 12, which is between about 4.98 and 4.99 nm.

As can be seen from these results of the simulations, radially polarized light gives a smoother distribution of overly values for each pixel, leading to a small standard deviation and therefore a closer result to the actually overlay result. Many simulations have been carried out using other models of the stack or pattern (shown in FIG. 9) and different overlay values including large overlay values up to about 30 nm, as well as different wavelengths of measurement radiation. In every case, significant improvement of the standard deviation has been observed and the mean overlay value has been seen to been closer to the real overlay.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track which is a tool that typically applies a layer of resist to a substrate and develops the exposed resist, a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

Conclusion

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional storing blocks illustrating the implementation of specified functions and relationships thereof. The boundaries of these functional storing blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A scatterometer, comprising:
   a radiation source configured to provide a radiation beam;
      a high numerical aperture lens configured to direct the radiation beam onto a substrate; and
   a detector configured to detect an angle-resolved spectrum of the radiation beam reflected at a plurality of angles from a surface of the substrate,
      wherein the radiation source is configured to radially polarize the radiation beam.

2. The scatterometer of claim 1, wherein the radiation source comprises a liquid nematic cell configured to polarize the radiation beam.

3. The scatterometer of claim 1, further comprising:
   an optical system configured to focus the radially polarized radiation beam to a focal spot with a diameter of up to about 200 nm.

4. The scatterometer of claim 1, wherein:
   the detector is configured to measure an overlay of a first layer on a substrate with respect to a second layer superimposed onto the first layer; and
   the detector is configured to detect at least the zeroth and first orders of the angle-resolved spectrum of the radially polarized radiation beam having been reflected from the superimposed first and second layers and to output an image of the respective intensities of the zeroth, −1 and +1 diffraction orders, a parameter of the image indicating the extent of the overlay.

5. The scatterometer of claim 4, wherein the parameter of the image indicating the extent of the overlay comprises a value on one of a color or gray-scale pixel image.

6. The scatterometer of claim 1, wherein the detector is configured to measure the property of the substrate by further measuring, substantially simultaneously, in the pupil plane of the high numerical aperture lens, a property of the reflected spectrum at a plurality of wavelengths.

7. The scatterometer of claim 1, wherein the lens comprises a numerical aperture of at least about 0.9.

8. The scatterometer of claim 1, further comprising a space between the substrate and the high numerical aperture lens containing a liquid.

9. The scatterometer of claim 1, wherein the radiation source comprises a polarizer configured to radially polarize the radiation beam.

10. The scatterometer of claim 1, wherein a critical dimension of a structure on the substrate is measured by measuring features in the reflected spectrum, the features being comparable to a library of predetermined features associated with known critical dimensions.

11. The scatterometer of claim 1, wherein the features in the reflected spectrum include asymmetry.

12. A method, comprising
   generating a pattern for printing onto a substrate through patterning a radially polarized radiation beam; and
   measuring, in the pupil plane of a high numerical aperture lens, a reflected spectrum of the pattern.

13. The method of claim 12, wherein the measuring the reflected spectrum comprises measuring (a) a property of the reflected spectrum at a plurality of angles, (b) a plurality of wavelengths, or both (a) and (b) simultaneously.

14. The method of claim 12, wherein:
   the pattern comprises two gratings layered in parallel and misaligned, thereby creating an overlay of one grating with respect to the other;
   wherein the measuring of the reflected spectrum of the gratings is carried out using a scatterometer; and
   wherein the extent of the overlay is derived from the asymmetry in the reflected spectrum.

15. A lithographic apparatus comprising:
   an illumination optical system configured to illuminate a pattern;
   a projection optical system configured to project an image of the pattern on to a substrate; and
   an angularly resolved scatterometer configured to measure a property of the substrate, the scatterometer comprising,
      a radiation source configured to provide a radiation beam,
      a high numerical aperture lens configured to direct the radiation beam on the substrate, and
      a detector configured to detect an angle-resolved spectrum of the radiation beam reflected at a plurality of angles from a surface of the substrate,
         wherein the radiation source is configured to radially polarize the radiation beam.

16. A lithographic cell, comprising:
   a coater configured to coat substrates with a radiation sensitive layer;
   a lithographic apparatus configured to expose images onto the radiation sensitive layer of substrates coated by the coater;
   a developer configured to develop images exposed by the lithographic apparatus; and
   an angularly resolved scatterometer configured to measure a property of a substrate, the scatterometer comprising,
      a radiation source configured to provide a radiation beam,
      a high numerical aperture lens, and a detector configured to detect an angle-resolved spectrum of the radiation beam reflected at a plurality of angles from a surface of the substrate,
wherein the radiation source is configured to radially polarize the radiation beam.

17. A device manufacturing method, comprising:

forming a pattern on a substrate using a lithographic apparatus; and determining a value related to a parameter of the pattern printed by:
providing a radiation beam;
generating a pattern for printing onto the substrate; and
measuring, in the pupil plane of a high numerical aperture lens, a reflected spectrum of the pattern, the reflected spectrum being created by the reflection of a radially polarized radiation beam from the pattern on the substrate.

* * * * *